(12) United States Patent
Rodgers et al.

(10) Patent No.: US 6,177,407 B1
(45) Date of Patent: Jan. 23, 2001

(54) METHODS TO INCREASE BLOOD FLOW TO ISCHEMIC TISSUE

(75) Inventors: Kathleen E. Rodgers, Long Beach; Gere DiZerega, Pasadena, both of CA (US)

(73) Assignee: University of Southern California

( * ) Notice: Under 35 U.S.C. 154(b), the term of this patent shall be extended for 0 days.

(21) Appl. No.: 09/373,962

(22) Filed: Aug. 13, 1999

Related U.S. Application Data

(60) Provisional application No. 60/096,414, filed on Aug. 13, 1999, and provisional application No. 60/101,024, filed on Sep. 18, 1998.

(51) Int. Cl.$^7$ .......................... A61K 38/06; A61K 38/07; A61K 38/08
(52) U.S. Cl. .................. 514/15; 514/16; 514/17; 514/18; 530/316
(58) Field of Search .............. 530/316; 514/15, 514/16, 17, 18

(56) References Cited

U.S. PATENT DOCUMENTS

| | | | |
|---|---|---|---|
| 4,296,100 | * 10/1981 | Franco | 514/21 |
| 4,956,455 | * 9/1990 | Esch et al. | 530/399 |
| 5,015,629 | * 5/1991 | DiZerega | 514/16 |
| 5,244,460 | 9/1993 | Unger et al. | 604/53 |
| 5,318,957 | 6/1994 | Cid | 514/8 |
| 5,589,173 | 12/1996 | O'Brien et al. | 424/145.1 |
| 5,629,292 | * 5/1997 | Rodgers et al. | 514/16 |
| 5,693,616 | 12/1997 | Krstenansky et al. | 514/12 |
| 5,716,935 | * 2/1998 | Rodgers et al. | 514/16 |
| 5,834,432 | * 11/1998 | Rodgers et al. | 514/16 |
| 5,955,430 | * 9/1999 | Rodgers et al. | 514/16 |

FOREIGN PATENT DOCUMENTS

| | | |
|---|---|---|
| WO 94/00492 | 1/1994 | (WO) . |
| WO 95/08337 | 3/1995 | (WO) . |
| WO 95/08565 | 3/1995 | (WO) . |
| WO 96/14858 | 5/1996 | (WO) . |
| WO 96/39164 | 12/1996 | (WO) . |
| 98/26795 | * 6/1998 | (WO) . |
| WO 98/26795 | 6/1998 | (WO) . |
| WO 98/32457 | 7/1998 | (WO) . |
| WO 98/33813 | 8/1998 | (WO) . |
| WO 99/26644 | 6/1999 | (WO) . |
| WO 99/31125 | 6/1999 | (WO) . |
| WO 99/40106 | 8/1999 | (WO) . |
| WO 99/40107 | 8/1999 | (WO) . |

OTHER PUBLICATIONS de Largen et al. Effects of Angiotensin II and Captopril . . . J. Cardiovascular Pharmacology, vol. 13, No. 2, pp. 186–191, 1989.*
Maeda. Nucleotide Sequence of the Haptoglobin . . . J. Biol. Chem. vol. 260, No. 11, pp. 6698–6709, Jun. 10, 1985.*
Folkman, et al., (1987), Science, 235: pp. 442–447.
Tyagi, (1997), J. Cell. Biochem., 65: pp. 388–394.
Pfeffer, (1991), Am. J. Cardiol., 68: pp. 127D–131D.
Hammermeister, et al., (1979), Circulation, 59: pp. 421–435.
Kim and Braunwald, (1993), Circulation, 88: pp. 2426–2436.
Hochman, et al., (1987), Circulation, 75: pp. 299–306.
Bonaduce, et al., (1990), J. Am. Coll. Cardiol., 16: pp. 1561–1568.

(List continued on next page.)

* cited by examiner

*Primary Examiner*—Jeffrey E. Russel
(74) *Attorney, Agent, or Firm*—McDonnell, Boehnen Hulbert & Berghoff; David S. Harper

(57) ABSTRACT

The present invention provides methods and kits for increasing blood flow to ischemic tissue, comprising the administration of an effective amount of angiotensinogen, angiotensin I (AI), AI analogues, AI fragments and analogues thereof, angiotensin II (AII), AII analogues, AII fragments or analogues thereof or AII $AT_2$ type 2 receptor agonists.

8 Claims, 3 Drawing Sheets

OTHER PUBLICATIONS

Fernandez, et al., (1982), Am. J. Physiol., 243: pp. H869–H875.
Shanugam, et al., (1995), Am. J. Physiol., 268: pp. F922–F930.
Helin, et al., (1997), Annals of Medicine, 29: pp. 23–29.
Bedecs, et al., (1997), Biochem J., 325: pp. 449–454.
Steckelings, et al., (1996), Biochem. Biophys. Res. Commun., 229: pp. 329–333.
Ferrario, et al., (1998), J. Am. Soc. Nephrol., 9: pp. 1716–1722.
Iyer, et al., (1998), Hypertension, 31: pp. 699–705.
Freeman, et al., (1996), 28: pp. 104–108.
Ambuhl, et al., (1994), Brain Res. Bull., 35: (4) pp. 289–291.
Dr. Zoltán Szekanecz, et al., (1998), Orvosi hetilap. Publisher Budapest: Orvos–Egészségügyi Dolgozók Szakservezete., lsb/sn/cdn 0030–6002, 139:(5), pp. 227–234.
Clouston, et al., (1988), Genomics, 2: pp. 240–248.
Kageyama, et al., (1984), Biochemistry, 23: pp. 3603–3609.
Ohkubo, et al., (1983), Proc. Natl. Acad. Sci., 80: pp. 2196–2200.
Dzau, et al., (1989), J. Mol. Cell. Cardiol., 21:S7 (Supp III).
Berk, et al., (1989), Hypertension, 13: (4) pp. 305–314.
Kawahara, et al., (1988), BBRC, 150: (1) pp. 52–59.
Naftilan, et al., (1989), J. Clin. Invest., 83: pp. 1419–1423.
Taubman, et al., (1989), J. Biol. Chem., 264: (1) pp. 526–530.
Nakahara, et al., (1992), BBRC, 184: (2) pp. 811–818.
Stouffer and Owens, (1992), Circ. Res., 70: (4) pp. 820–828.
Wolf, et al., (1992), Am. J. Pathol., 140:(1) pp. 95–107.
Bell and Madri, (1990), Am. J. Pathol., 137: pp. 7–12.
Fernandez, et al., (1985), J. Lab. Clin. Med., 105: (2) pp. 141–145.
LeNoble, et al., (1991), Eur. J. Pharmacol., 195: pp. 305–306.
Speth and Kim, (1990), BBRC, 169: pp. 997–1006.
Catalioto, et al., (1994), Eur. J. Pharmacol., 256: 93–97.
Bryson, et al., (1992), Eur. J. Pharmacol., 225: pp. 119–127.
Janiak, et al., (1992), Hypertension, 20: pp. 737–745.
Prescott, et al., (1991), Am. J. Pathol., 139: pp. 1291–1296.
Kauffman, et al., (1991), Life Sci., 49: pp. 223–228.
Viswanathan, et al., (1992), Peptides, 13: pp. 783–786.
Kimura, et al., (1992), BBRC, 187: pp. 1083–1090.
Pfeilschifter, et al., (1992), Eur. J. Pharmacol., 225: pp. 57–62.
Jaiswal, et al., (1992), Hypertension 19, Supp. II: II–49—II–55.
Edwards and Stack, (1993), J. Pharmacol. Exper. Ther., 266: pp. 506–509.
Jaiswal, et al., (1993), J. Pharmacol. Exper. Ther., 265: pp. 664–673.
Jaiswal, et al., (1991), Hypertension, 17: pp. 1115–1119.
Portsi, et al., (1994), Br. J. Pharmacol, 111: pp. 652–654.
Regoli, et al., (1974), Pharmacological Reviews, 26: pp. 69–123.

SEQUENCE LISTING

<160> NUMBER OF SEQ ID NOS: 42

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:AII

<400> SEQUENCE: 1

Asp Arg Val Tyr Ile His Pro Phe
 1               5

<210> SEQ ID NO 2
<211> LENGTH: 7
<212> TYPE: PRT
<213> ORGANISM: Artificial Sequence -continued

```
<220> FEATURE:
<223> OTHER INFORMATION: Description of Artificial Sequence:AII (2-8)

<400> SEQUENCE: 2

Arg Val Tyr Ile His Pro Phe
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:AII (3-8)

<400> SEQUENCE: 3

Val Tyr Ile His Pro Phe
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:AII (1-7)

<400> SEQUENCE: 4

Asp Arg Val Tyr Ile His Pro
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:AII (2-7)

<400> SEQUENCE: 5

Arg Val Tyr Ile His Pro
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:AII (3-7)

<400> SEQUENCE: 6

Val Tyr Ile His Pro
 1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:AII (5-8)

<400> SEQUENCE: 7

Ile His Pro Phe
 1

<210> SEQ ID NO 8
<211> LENGTH: 6
<212> TYPE: PRT
<213> ORGANISM: Artificial Sequence
<220> FEATURE:
```

```
<223> OTHER INFORMATION: Description of Artificial Sequence:AII (1-6)

<400> SEQUENCE: 8

Asp Arg Val Tyr Ile His
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:AII (1-5)

<400> SEQUENCE: 9

Asp Arg Val Tyr Ile
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:AII (1-4)

<400> SEQUENCE: 10

Asp Arg Val Tyr
 1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence:AII (1-3)

<400> SEQUENCE: 11

Asp Arg Val
 1

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:AII analogue
<220> FEATURE:
<221> NAME/KEY: MOD_RES
<222> LOCATION: (2)
<223> OTHER INFORMATION: Nle

<400> SEQUENCE: 12

Arg Xaa Tyr Ile His Pro Phe
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:AII analogue
<220> FEATURE:
<221> NAME/KEY: MOD_RES
<222> LOCATION: (4)
<223> OTHER INFORMATION: Nle

<400> SEQUENCE: 13

Arg Val Tyr Xaa His Pro Phe
 1               5
```

```
<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence:AII (6-8)

<400> SEQUENCE: 14

His Pro Phe
  1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:AII (4-8)

<400> SEQUENCE: 15

Tyr Ile His Pro Phe
  1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:AII analogue
      class
<220> FEATURE:
<221> NAME/KEY: UNSURE
<222> LOCATION: (1)
<223> OTHER INFORMATION: Xaa at position 1 can be Arg, Lys, Ala, Orn,
      Ser, MeGly, D-Arg, or D-Lys
<220> FEATURE:
<221> NAME/KEY: UNSURE
<222> LOCATION: (2)
<223> OTHER INFORMATION: Xaa at position 2 can be Val, Ala, Leu, Nle,
      Ile, Gly, Pro, Aib, Acp, or Tyr
<220> FEATURE:
<221> NAME/KEY: UNSURE
<222> LOCATION: (4)
<223> OTHER INFORMATION: Xaa at position 4 can be Ile, Ala, Leu, Nle,
      Val, or Gly

<400> SEQUENCE: 16

Xaa Xaa Tyr Xaa His Pro Phe
  1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 17

Arg Val Tyr Gly His Pro Phe
  1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 18
```

Arg Val Tyr Ala His Pro Phe
  1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:AII analogue
      1

<400> SEQUENCE: 19

Asp Arg Val Tyr Val His Pro Phe
  1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence:AII analogue
      2

<400> SEQUENCE: 20

Asn Arg Val Tyr Val His Pro Phe
  1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence:AII analogue
      3

<400> SEQUENCE: 21

Ala Pro Gly Asp Arg Ile Tyr Val His Pro Phe
  1               5                  10

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:AII analogue
      4

<400> SEQUENCE: 22

Glu Arg Val Tyr Ile His Pro Phe
  1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence:AII analogue
      5

<400> SEQUENCE: 23

Asp Lys Val Tyr Ile His Pro Phe
  1               5

<210> SEQ ID NO 24
<211> LENGTH: 8
<212> TYPE: PRT
<213> ORGANISM: Artificial Sequence
<220> FEATURE:

```
<223> OTHER INFORMATION: Description of Artificial Sequence:AII analogue
      6

<400> SEQUENCE: 24

Asp Arg Ala Tyr Ile His Pro Phe
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:AII analogue
      7

<400> SEQUENCE: 25

Asp Arg Val Thr Ile His Pro Phe
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence:AII analogue
      8

<400> SEQUENCE: 26

Asp Arg Val Tyr Leu His Pro Phe
 1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence:AII analogue
      9

<400> SEQUENCE: 27

Asp Arg Val Tyr Ile Arg Pro Phe
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:AII analogue
      10

<400> SEQUENCE: 28

Asp Arg Val Tyr Ile His Ala Phe
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:AII analogue
      11

<400> SEQUENCE: 29

Asp Arg Val Tyr Ile His Pro Tyr
 1               5
```

```
<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:AII analogue
      12

<400> SEQUENCE: 30

Pro Arg Val Tyr Ile His Pro Phe
  1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:AII analogue
      13

<400> SEQUENCE: 31

Asp Arg Pro Tyr Ile His Pro Phe
  1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:AII analogue
      14
<220> FEATURE:
<221> NAME/KEY: MOD_RES
<222> LOCATION: (4)
<223> OTHER INFORMATION: PHOSPHORYLATION

<400> SEQUENCE: 32

Asp Arg Val Tyr Ile His Pro Phe
  1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:AII analogue
      15
<220> FEATURE:
<221> NAME/KEY: MOD_RES
<222> LOCATION: (3)
<223> OTHER INFORMATION: Nle

<400> SEQUENCE: 33

Asp Arg Xaa Tyr Ile His Pro Phe
  1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:AII analogue
      16
<220> FEATURE:
<221> NAME/KEY: MOD_RES
<222> LOCATION: (5)
<223> OTHER INFORMATION: Nle

<400> SEQUENCE: 34

Asp Arg Val Tyr Xaa His Pro Phe
```

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:AII analogue
      17
<220> FEATURE:
<221> NAME/KEY: MOD_RES
<222> LOCATION: (4)
<223> OTHER INFORMATION: homo Ser

<400> SEQUENCE: 35

Asp Arg Val Ser Tyr Ile His Pro Phe
 1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial
      Sequence:p-aminophenylalanine 6 AII
<220> FEATURE:
<221> NAME/KEY: MOD_RES
<222> LOCATION: (6)
<223> OTHER INFORMATION: p-aminophenylalanine

<400> SEQUENCE: 36

Asp Arg Val Tyr Ile Xaa Pro Phe
 1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence:angiotensin
      I

<400> SEQUENCE: 37

Asp Arg Val Tyr Ile His Pro Phe His Leu
 1               5                  10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:1GD:
      Ala4-AII(1-7)

<400> SEQUENCE: 38

Asp Arg Val Ala Ile His Pro
 1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence:2GD:
      Pro3-AII(1-7)

<400> SEQUENCE: 39

Asp Arg Pro Tyr Ile His Pro
 1               5

```
<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence:5GD:
      Lys3-AII(1-7)

<400> SEQUENCE: 40

Asp Arg Lys Tyr Ile His Pro
1               5

<210> SEQ ID NO 41
<211> LENGTH: 7
<212> TYPE: PRT
<213> ORGANISM: Artificial Sequence
<220> FEATURE:
<221> NAME/KEY: MOD_RES
<222> LOCATION: (3)
<223> OTHER INFORMATION: Nle
<220> FEATURE:
<223> OTHER INFORMATION: Description of Artificial Sequence:9GD:
      norLeu3-AII(1-7)

<400> SEQUENCE: 41

Asp Arg Xaa Tyr Ile His Pro
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence:Ile8-AII

<400> SEQUENCE: 42

Asp Arg Val Tyr Ile His Pro Ile
1               5
```

US 6,177,407 B1

METHODS TO INCREASE BLOOD FLOW TO ISCHEMIC TISSUE

CROSS REFERENCE

This application claims the benefit of U.S. Provisional Application Nos. 60/096,414 filed Aug. 13, 1998 and 60/101,024 filed Sep. 18, 1998.

BACKGROUND OF THE INVENTION

Collateral circulation to tissues can be stimulated in two independent ways: 1) the formation of new blood vessels through angiogenesis and 2) the enhancement in function of preexisting blood vessels (Fernandez et al., *J. Lab. Clin. Med.* 105:141–145 (1985)).

Angiogenesis is the process by which new blood vessels are formed from existing capillaries. (U.S. Pat. No. 5,318,957, incorporated by reference herein in its entirety.) Angiogenesis plays an important role in such widely divergent biological conditions as embryonic development, tumor growth, wound healing, and chronic inflammatory disease. (Folkman et al., *Science* 235:442–447 (1987))

Capillaries are composed almost entirely of endothelial cells. Angiogenesis comprises a cascade of events, including protease secretion by endothelial cells, degradation of the basement membrane, migration through the surrounding matrix, proliferation, alignment, differentiation into tube-like structures, and synthesis of a new basement membrane. (U.S. Pat. No. 5,318,957)

Several angiogenic agents with different properties and mechanisms of action are well known in the art, including acidic and basic fibroblast growth factor, transforming growth factor alpha and beta, tumor necrosis factor, platelet-derived growth factor, vascular endothelial growth factor, angiogenin, and haptoglobin. (U.S. Pat. No. 5,318,957) However, the therapeutic applicability of some of these compounds is limited by their potent pleiotropic effects on various cell types. Thus, there remains a need in the art for angiogenic agents with more general applicability.

Very few therapies have been demonstrated to increase collateral circulation by enhancing the function of existing blood vessels. In an isolated case, U.S. Pat. No. 4,296,100 discloses animal experiments wherein bovine fibroblast growth factor (FGF) was injected into the heart to distribute the desired amount of FGF over the area of the heart to be treated. This treatment was given as close to the time the heart attack as possible in order to control damage, possibly by improving collateral circulation, although the exact mechanism is known. The experiments showed that a one time treatment could reduce infarct size (area that will scar or remain permanently damaged) in the test animal to one quarter the size of the control (non-treated) hearts. Histological studies did not show a significant increase in capillary areas in the hearts as a result of such treatment with FGF.

Congestive heart failure is the leading cause of cardiovascular mortality (Tyagi, *J. Cell Biochem.* 65:388–394. (1997), and is caused by cardiac remodeling that leads to an enlargement of the heart following a myocardial infarction (Pfeffer, *Am. J. Cardiol.* 68:17D–25D (1991)). There is a strong correlation between long term morbidity from congestive heart failure and the degree of post-infarct remodeling. As little as a 35% increase in the volume of the heart in the months following infarction leads to an increase in mortality by a factor of 3–4(Hammermeister et al., *Circulation* 59:421–435 (1979)). Therefore, therapies that attenuate cardiac remodeling following myocardial infarction are needed to prevent the development of congestive heart disease.

The loss of blood flow to the ischemic tissue is the primary factor in causing cardiac remodeling. Studies show that there is major cardiac remodeling following a myocardial infarction if the infarct-related artery is totally occluded (Kim and Braunwald, *Circulation* 88:2426–2436 (1993)). However, cardiac remodeling can be minimized if blood flow can be restored to the ischemic tissue. In addition, the earlier blood flow is restored the more cardiac remodeling can be attenuated (Hochman et al., *Circulation* 75:299–306 (1987); Bonaduce et al., *J. Am. Coll. Cardiol.* 16:1561–1568 (1990)). Therefore, treatments aimed at quickly restoring blood flow following myocardial infarction can minimize cardiac remodeling and the development of congestive heart disease.

Chemical therapies are currently one of the most useful treatments for restoring blood flow to ischemic tissue following myocardial infarction. Thrombolytic therapies are based on clearing the occluded coronary artery in order to restore blood flow (U.S. Pat. No. 5,589,173). In addition to clearing the occluded coronary artery, the presence of a collateral blood supply can minimize the effect of cardiac remodeling. Therefore, chemical therapies directed at stimulating collateral circulation could minimize cardiac remodeling following myocardial infarction. However, there are currently few materials available for stimulating collateral blood flow.

Based on the above, there remains a need for the development of methods to increase blood flow to ischemic tissue in general, and a particular need for increasing blood flow to the heart following a myocardial infarction.

SUMMARY OF THE INVENTION

The present invention provides improved methods and kits to increase blood flow to ischemic tissue comprising the administration of angiotensinogen, angiotensin I (AI), AI analogues, AI fragments and analogues thereof, angiotensin II(AII) analogues, AII fragments or analogues thereof or AII $AT_2$ type 2 receptor agonists.

DETAILED DESCRIPTION OF THE PREFERRED EMBODIMENTS

Figure 1:
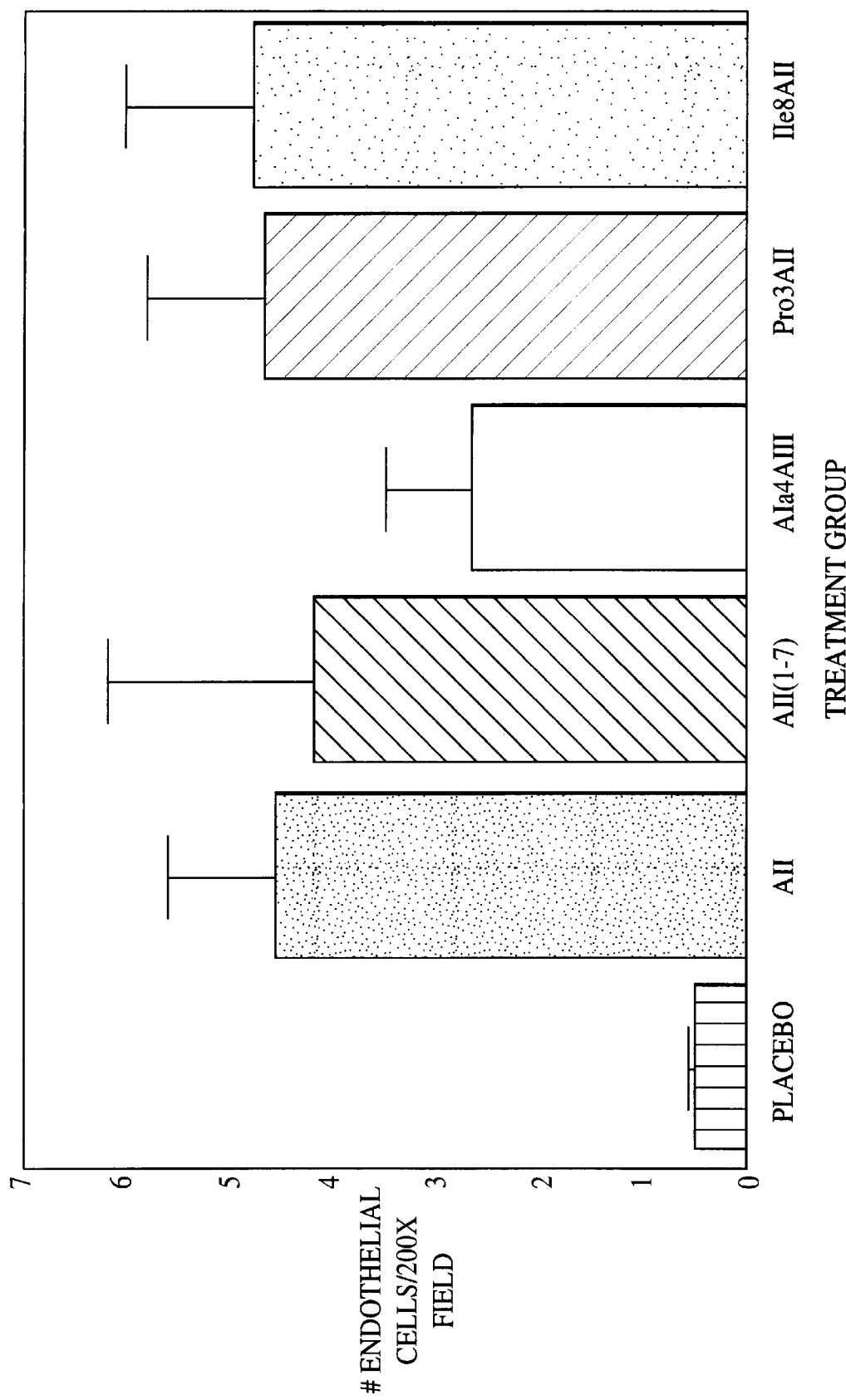
FIG. 1 is a graph showing the effect of AII analogues on blood flow in conjunction with Apligraf treatment.

All references, patents and patent applications are hereby incorporated by reference in their entirety.

As used herein, the term "ischemia" refers to any condition associated with an inadequate flow of oxygenated blood to a part of the body. Ischemia occurs any time that blood flow to a tissue is reduced below a critical level. This reduction in blood flow can result from the following non-limiting conditions: (i) the blockage of a vessel by an embolus (blood clot); (ii) the blockage of a vessel due to atherosclerosis; (iii) the breakage of a blood vessel (a bleeding stroke); (iv) the blockage of a blood vessel due to vasoconstriction such as occurs during vasospasms and possibly, during transient ischemic attacks (TIA) and following subarachnoid hemorrhage. Further conditions in which ischemia occurs, include (i) during myocardial infarction (when the heart stops, the flow of blood to organs is reduced and ischemia results); (ii) trauma; and (iii) during cardiac and neurosurgery (blood flow needs to be reduced or stopped to achieve the aims of surgery).

As used herein, the term "ischemic tissue" refers to any tissue that is receiving an inadequate flow of oxygenated blood.

As used herein, "increasing blood flow" refers to such increases mediated by either the formation of new blood vessels through angiogenesis or the enhancement in function of preexisting blood vessels.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.) "Guide to Protein Purification" in *Methods in Enzymology* (M. P. Deutshcer, ed., (1990) Academic Press, Inc.): *PCR Protocols: A guide to Methods and Applications* (Innis, Et al. 1990. Academic Press, San Diego, Calif.), *Culture of Animal Cells: A Manual of Basic Technique, 2$^{nd}$ Ed.* (R. I. Freshney. 1987. Liss, Inc. New York, N.Y.), *Gene Transfer and Expression Protocols*, pp. 109–128, ed. E. J. Murray, The Humana Press Inc., Clifton, N.J.), and the Ambion 1998 Catalog (Ambion, Austin, Tex.).

U.S. Pat. No. 5,015,629 to DiZerega (the entire disclosure of which is hereby incorporated by reference ) describes a method for increasing the rate of healing of wound tissue, comprising the application to such tissue of angiotensin II (AII) in an amount which is sufficient for said increase. The application of AII to wound tissue significantly increases the rate of wound healing, leading to a more rapid re-epithelialization and tissue repair. The term AII refers to an octapeptide present in humans and other species having the sequence Asp-Arg-Val-Tyr-Ile-His-Pro- [SEQ ID NO:1]. The biological formation of angiotensin is initiated by the action of renin on the plasma substrate angiotensinogen (Clouston et al., *Genomics* 2:240–248 (1988); Kageyama et al, *Biochemistry* 23:3603–3609; Ohkubo et al., *Proc. Natl. Acad. Sci.* 80:2196–2220 (1983); each reference hereby incorporated in its entirety). The substance so formed is a decapeptide called angiotensin I (AI) which is converted to AII by the angiotensin converting enzyme (ACE) which removes the C-terminal His-Leu residues from AI[SEQ ID NO. 37]. AII is a known pressor agent and is commercially available.

Studies have shown that AII increases mitogenesis and chemotaxis in cultured cells that are involved in wound repair, and also increases their release of growth factors and extracellular matrices (diZerega, U.S. Pat. No. 5,015,629; Dzau et. al., *J. Mol. Cell. Cardiol.* 21:S7 (Supp III) 1989; Berk et. al., *Hypertension* 13:305–14 (1989); Kawahara, et al., *BBRC* 150:52–9 (1988); Naftilan, et al., *J. Clin. Invest.* 83:1419–23 (1989); Taubman et al., *J. Biol. Chem.* 264:526–530 (1989); Nakahara, et al., *BBRC* 184:811–8 (1992); Stouffer and Owens, *Circ. Res.* 70:820 (1992); Wolf, et a.,*Am. J. Pathol.* 140:95–107 (1992); Bell and Madri,*Am. J. Pathol.* 137:7–12 (1990). In addition, AII was shown to be angiogenic in rabbit corneal eye and chick chorioallantoic membrane models (Fernandez, et al., *J. Lab. Clin. Med.* 105:141 (1985); LeNoble, et al., *Eur. J. Pharmacol.* 195:305–6 (1991). Additionally, AII and angiotensin III analogs and fragments, and AII Type 2 receptor agonsists thereof have been shown to be effective in wound healing. (U.S. Pat Nos. 5,629,292; 5,716,935; International Application Nos. WO 95/08565; WO 95/08337; WO 06/39164; all references hereby incorporated in their entirety.)

Angiotensin II is also known as a potent stimulator of angiogenesis (Fernandez et al., *J. Lab. Clin. Med.* 105:141–145 (1985)), and has been shown to activate collateral circulation via preformed blood vessels in rat kidneys (Fernandez et al., *Am. J. Physiol.* 243:H869–H875 (1982)).

The effect of AII on a given cell type has been hypothesized to be dependent, in part, upon the AII receptor subtypes the cell expresses (Shanugam et al.,*Am. J. Physiol.* 268:F922–F930 (1995); Helin et al., *Annals of Medicine* 29:23–29 (1997); Bedecs et al., *Biochem J.* 325:449–454 (1997)). These studies have shown that AII receptor subtype expression is a dynamic process that changes during development, at least in some cell types (Id.). AII activity is typically modulated by either or both the AT1 and AT2 II receptors. However, AII has recently been shown to stimulate proliferation of primary human keratinocytes via a non-AT1, non-AT2 receptor. (Steckelings et al., Biochem. Biophys. Res. Commun. 229:329–333 (1996). These results underscore the cell-type (i.e.: based on receptor expression) specific nature of AII activity.

Other data suggests that the AII fragment AII(1–7) acts through a receptor(s) that is distinct from the AT1 and AT2 receptors which modulate AII activity. (Ferrario et al., J. Am. Soc. Nephrol. 9:1716–1722 (1998); Iyer et al., Hypertension 31:699–705 (1998); Freeman et al., Hypertension 28:104 (1996); Ambuhl et al., Brain Res. Bull. 35:289 (1994). Thus, AII(1–7) activity, on a particular cell type cannot be predicted based solely on the effect of AII on the same cell type.

However, based on all of the above, it is unknown whether the use of angiotensinogen, angiotensin I(AI), AI analogues, AI fragments and analogues thereof, ALL analogues, AII fragments or analogues thereof or AII AT$_2$ type 2 receptor (AT2) agonists would be effective in stimulating blood flow to ischemic tissue. The identification of AII analogues and fragments that stimulate blood flow with fewer side effects than AII would be extremely beneficial.

A peptide agonist selective for the AT2 receptor (AII has 100 times higher affinity for AT2 than AT1) has been identified. This peptide is p-aminophenylalanine 6-AII ["(p-NH$_2$-Phe)6-AII)"], Asp-Arg-Val-Tyr-Ile-Xaa-Pro-Phe [SEQ ID NO.36] wherein Xaa is p-NH$_2$-Phe (Speth and Kim, BBRC 169:997–1006 (1990). This peptide gave binding characteristics comparable to AT2 antagonists in the experimental models tested (Catalioto, et al., *Eur. J. Pharmacol.* 256:93–97 (1994); Bryson, et al., *Eur. J. Pharmacol.* 225:119–127 (1992).

The effects of AII receptor and AII receptor antagonists have been examined in two experimental models of vascular injury and repair which suggest that both AII receptor subtypes (AT1 and AT2) play a role in wound healing (Janiak et al., *Hypertension* 20:737–45 (1992); Prescott, et al., *Am. J. Path.* 139:1291–1296 (1991); Kauffman, et al., *Life Sci.* 49:223–228 (1991); Viswanathan, et al., *Peptides* 13:783–786 (1992); Kimura, et al., *BBRC* 197:1083–1090 (1992).

Many studies have focused upon AII(1–7) (AII residues 1–7) or other fragments of AII to evaluate their activity. AII(1–7) elicits some, but not the full range of effects elicited by AII. Pfeilschifter, et al., *Eur. J. Pharmacol.* 225:57–62 (1992); Jaiswal, et al., *Hypertension* 19(Supp.

II)II-49–II-55 (1992); Edwards and Stack, *J. Pharmacol. Exper. Ther.* 266:506–510 (1993); Jaiswal, et al., *J. Pharmacol. Exper. Ther.* 265:664–673 (1991); Jaiswal, et al., *Hypertension* 17:1115–1120 (1991); Portsi, et a., *Br. J. Pharmacol.* 111:652–654 (1994).

As hereinafter defined, a preferred class of AT2 agonists for use in accordance with the present invention comprises angiotensinogen, angiotensin I(AI), AI analogues, AI fragments and analogues thereof, AII analogues, AII fragments or analogues thereof or AII $AT_2$ type 2 receptor agonists having p-NH-Phe in a position corresponding to a position 6 of AII. In addition to peptide agents, various nonpeptidic agents (e.g., peptidomimetics) having the requisite AT2 agonist activity are further contemplated for use in accordance with the present invention.

The active AII analogues, fragments of AII and analogues thereof of particular interest in accordance with the present invention comprise a sequence consisting of at least three contiguous amino acids of groups $R^1-R^8$ in the sequence of general formula I:

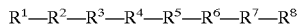

in which $R^1$ and $R^2$ together form a group of formula

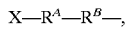

wherein X is H or a one to three peptide group, or is absent, $R^A$ is suitably selected from H, Asp, Glu, Asn, Acpc (1-aminocyclopentane carboxylic acid), Ala, Me²Gly, Pro, Bet, Glu(NH₂), Gly, Asp(NH₂) and Suc, $R^B$ is suitably selected from Arg, Lys, Ala, Orn, Citron, Ser(Ac), Sar, D-Arg and D-Lys;

$R^3$ is selected from the group consisting of Val, Ala, Leu, norLeu, Ile, Gly, Pro, Aib, Acpc and Tyr;

$R^4$ is selected from the group consisting of Tye, Tyr(PO₃)₂, Thr, Ala, Ser, homoSer and azaTyr;

$R^5$ is selected from the group consisting of Ile, Ala, Leu, norLeu, Val and Gly;

$R^6$ is His, Arg or 6-NH₂-Phe;

$R^7$ is Pro or Ala; and $R^8$ is selected from the group consisting of Phe, Phe(Br), Ile and Tyr, excluding sequences including $R^4$ as a terminal Tyr group, or is absent, wherein the active agent is not AII.

Compounds falling within the category of AT2 agonists useful in the practice of the invention include the AII analogues set forth above subject to the restriction that $R^6$ is p-NH₂-Phe.

Particularly preferred combinations for $R^A$ and $R^B$ are Asp-Arg, Asp-Lys, Glu-Arg and Glu-Lys. Particularly preferred embodiments of this class include the following: AIII or AII(2–8), Arg-Val-Tyr-Ile-His-Pro-Phe [SEQ ID NO:2]; AII(3–8), also known as des1-AIII or AIV, Val-Tyr-Ile-His-Pro-Phe [SEQ ID NO:3]; AII(1–7), Asp-Arg-Val-Tyr-Ile-His-Pro [SEQ ID NO:4]; AII(2–7). Arg-Val-Tyr-Ile-His-Pro [SEQ ID NO:5]; AII(3–7), Val-Tyr-Ile-His-Pro [SEQ ID NO:6]; AII(5–8), Ile-His-Pro-Phe [SEQ ID NO:7];AII(1–6), Asp-Arg-Val-Tyr-Ile-His [SEQ ID NO:8]; AII(1–5), Asp-Arg-Val-Tyr-Ile [SEQ ID NO:9]; AII(1–4), Asp-Arg-Val-Tyr [SEQ ID NO:10]; and AII(1–3), Asp-Arg-Val [SEQ ID NO:11]. Other preferred embodiments include: Arg-norLeu-Tyr-Ile-His-Pro-Phe [SEQ ID NO:12] and Arg-Val-Tyr-norLeu-His-Pro-Phe [SEQ ID NO:13]. Still another preferred embodiment encompassed within the scope of the invention is a peptide having the sequence Asp-Arg-Pro-Tyr=Ile-His-Pro-Phe [SEQ ID NO:15] were also tested and found not to be effective.

In a particularly preferred embodiment, the active compounds of the present invention are selected from those comprising the following general formula:

R1-Arg-R2-R3-R4-His-Pro-R5, wherein

R1 is Asp or is absent;

R2 is selected from the group consisting of Val, Ala, Ile, Pro, Lys, Norleu, and Leu;

R3 is selected from the group consisting of Ala, Tyr, and Tyr(PO₃)₂; and

R4 is selected from the group consisting of Val, Ala, Ile, Norleu, and Leu;

R5 is Phe, Ile, or is absent;

wherein the compound is no AII.

In a most particularly preferred embodiment, the active compound is selected from the group consisting of SEQ ID NO:4, SEQ ID NO:19, SEQ ID NO:24, SEQ ID NO:26, SEQ ID NO:31, SEQ ID NO:32, SEQ ID NO:33, SEQ ID NO:34, SEQ ID NO:38, SEQ ID NO:39, SEQ ID NO:40, SEQ ID NO:41, and SEQ ID NO:42.

Another class of compounds of particular interest in accordance with the present invention are those of the general formula II:

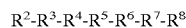

in which $R^2$ is selected from the group consisting of H, Arg, Lys, Ala, Orn, Citron, Ser(Ac), Sar, D-Arg and D-Lys;

$R^3$ is selected from the group consisting of Val, Ala, Leu, norLeu, Ile, Gly, Pro, Aib, Acpc and Tyr;

$R^4$ is selected from the group consisting of Tyr, Tyr(PO₃)₂, Thr, Ser, homoSer, Ala, and azaTyr;

$R^5$ is selected from the group consisting of Ile, Ala, Leu, norLeu, Val and Gly;

$R^6$ is His, Arg or 6-HN₂-Phe;

$R^7$ is Pro or Ala; and $R^8$ is selected from the group consisting of Phe, Phe(Br), Ile and Tyr.

A particularly preferred subclass of the compounds of general formula II has the formula R²-R³-Tyr-R⁵-His-Pro-Phe [SEQ ID NO:16]

wherein $R^2$, $R^3$ and $R^5$ are as previously defined. Particularly preferred is angiotensin III of the formula Arg-Val-Tyr-Ile-His-Pro-Phe [SEQ ID NO:2]. Other preferred compounds include peptides having the structures Arg-Val-Tyr-Gly-His-Pro-Phe [SEQ ID NO:17] and Arg-Val-Tyr-Ala-His-Pro-Phe [SEQ ID NO:18]. The fragment AII(4–8) was ineffective in repeated tests; this is believed to be due to the exposed tyrosine on the N-terminus.

In the above formulas, the standard three-letter abbreviations for amino acid residues are employed. In the absence of an indication to the contrary, the L-form of the amino acid is intended. Other residues are abbreviated as follows:

TABLE 1

Abbreviation for Amino Acids

| | |
|---|---|
| Me²Gly | N,N-dimethylglycyl |
| Bet | 1,carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |
| Orn | Ornithine |

It has been suggested that AII and its analogues adopt either a gamma or a beta turn (Regoli, et al., *Pharmacological Reviews* 26:69 (1974). In general, it is believed that neutral side chains in position $R^3$, $R^5$ and $R^7$ may be involved in maintaining the appropriate distance between active groups in positions $R^4$, $R^6$ and $R^8$ primarily responsible for binding to receptors and/or intrinsic activity. Hydrophobic side chains in positions $R^3$, $R^5$ and $R^8$ may also play an important role in the whole conformation of the peptide and/or contribute to the formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$.

For purposes of the present invention, it is believed that $R^3$ may be involved in the formation of linear or nonlinear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Val, Ala, Leu, norLeu, Ile, Gly, Pro, Aib, Acpc and Tyr. $R^3$ may also suitably be Lys.

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Tyr $(PO_3)_2$, homoSer, Ser and azaTyr. In this position, Tyr is particularly preferred as it may form a hydrogen bond with the receptor site capable of accepting a hydrogen from the phenolic hydroxyl (Regoli, et al. (1974), supra). $R^4$ may also suitably be Ala.

In position $R^5$, an amino acid with a β aliphatic or alicyclic chain is particulary desirable. Therefore, while Gly is suitable in position $R^5$, it is preferred that the amino acid in this position be selected from Ile, Ala, Leu, norLeu, Gly and Val.

In the angiotensinogen, AI, AI analogues, AI fragments and analogues thereof, AII analogues, fragments and analogues of fragments of particular interest in accordance with the present invention, $R^6$ is His, Arg or 6-$NH_2$-Phe. The unique properties of the imidazole ring of histidine (e.g., ionization at physiological pH, ability to act as proton doner or acceptor, aromatic character) are believed to contribute to its particular utility as $R^6$. For example, conformation models suggest that His may participate in hydrogen bond formation (in the beta model) or in the second turn of the antiparallel structure by influencing the orientation of $R^7$. Similarly, it is presently considered that $R^7$ should be Pro in order to provide the most desirable orientation of $R^8$. In position $R^8$, both a hydrophobic ring and anionic carboxyl terminal appear to be particularly useful in binding of the analogues of interest to receptors; therefore, Tyr and especially Phe are preferred for purposes of the present invention. $R^8$ may also suitable be Ile.

Analogues of particular interest include the following:

TABLE 2

Angiotensin II Analogues

| AII Analogue Name | Amino Acid Sequence | Sequence Identifier |
|---|---|---|
| Analogue 1 | Asp-Arg-Val-Tyr-Val-His-Pro-Phe | SEQ ID NO: 19 |
| Analogue 2 | Asn-Arg-Val-Tyr-Val-His-Pro-Phe | SFQ ID NO: 20 |
| Analogue 3 | Ala-Pro-Gly-Asp-Arg-Ile-Tyr-Val-His-Pro-Phe | SEQ ID NO: 21 |
| Analogue 4 | Glu-Arg-Val-Tyr-Ile-His-Pro-Phe | SEQ ID NO: 22 |
| Analogue 5 | Asp-Lys-Val-Tyr-Ile-His-Pro-Phe | SEQ ID NO: 23 |
| Analogue 6 | Asp-Arg-Ala-Tyr-Ile-His-Pro-Phe | SEQ ID NO: 24 |
| Analogue 7 | Asp-Arg-Val-Thr-Ile-His-Pro-Phe | SEQ ID NO: 25 |
| Analogue 8 | Asp-Arg-Val-Tyr-Leu-His-Pro-Phe | SEQ ID NO: 26 |
| Analogue 9 | Asp-Arg-Val-Tyr-Ile-Arg-Pro-Phe | SEQ ID NO: 27 |
| Analogue 10 | Asp-Arg-Val-Tyr-Ile-His-Ala-Phe | SEQ ID NO: 28 |
| Analogue 11 | Asp-Arg-Val-Tyr-Ile-His-Pro-Tyr | SEQ ID NO: 29 |
| Analogue 12 | Pro-Arg-Val-Tyr-Ile-His-Pro-Phe | SEQ ID NO: 30 |

TABLE 2-continued

Angiotensin II Analogues

| AII Analogue Name | Amino Acid Sequence | Sequence Identifier |
|---|---|---|
| Analogue 13 | Asp-Arg-Pro-Tyr-Ile-His-Pro-Phe | SEQ ID NO: 31 |
| Analogue 14 | Asp-Arg-Val-Tyr(PO$_3$)$_2$-Ile-His-Pro-Phe | SEQ ID NO: 32 |
| Analogue 15 | Asp-Arg-norLeu-Tyr-Ile-His-Pro-Phe | SEQ ID NO: 33 |
| Analogue 16 | Asp-Arg-Val-Tyr-norLeu-His-Pro-Phe | SEQ ID NO: 34 |
| Analogue 17 | Asp-Arg-Val-homoSer-Tyr-Ile-His-Pro-Phe | SEQ ID NO: 35 |

The polypeptides of the instant invention may be synthezied by any conventional method, including, but not limited to, those set forth in J. M. Stewart and J. D. Young, Solid Phase Peptide Synthesis, 2nd ed., Pierce Chemical Co., Rockford, Ill.. (1984) and J. Meienhofer, Hormonal Proteins and Peptides, Vol. 2, Academic Press, New York (1973) for solid phase synthesis and E. Schroder and K. Lubke, The Peptides, Vol. 1, Academic Press, New York, (1965) for solution synthesis. The disclosures of the foregoing treatises and incorporated by reference herein.

In general, these methods involve the sequential addition of protected amino acids to a growing peptide chain (U.S. Pat. No. 5,693,616, herein incorporated by reference in its entirety). Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

Preferably, peptides are synthesized according to standard solid-phase methodologies, such as may be performed on an Applied Biosystems Model 430A peptide synthesized (Applied Biosystems, Foster City, Calif.), according to manufacturer's instructions. Other methods of synthesizing peptides or peptidomimetics, either by solid phase methodologies or in liquid phase, are well known to those skilled in the art.

In one aspect, the present invention provides methods and kits to increase blood flow to ischemic tissue, comprising the administration of angiotensinogen I (AI), AI analogues, AI fragments and analogues thereof, angiotensin II (AII) analogues, AII fragments or analogues thereof or AII AT$_2$ type 2 receptor agonists (Hereinafter referred to as the "active agents").

According to the invention, an area of ischemic tissue is treated in vivo to maintain viability of that area for a sustained period of time to salvage the area. An effective dose of the active agents is applied to the ischemic tissue, preferably after ischemia, although it can also be applied when there is an indication of impending ischemia.

The ischemic tissue is suitably any tissue that can benefit by an increased blood flow to the tissue to reverse or prevent the adverse effects of ischemia on the tissue. In preferred embodiments, the tissue is selected from skin and heart. In a further preferred embodiment, the active agents can be used to stimulate blood flow to tissue grafts, whether artificial or transplanted.

The active agents may be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intraarterial, intramuscular, intrasternal, intracardiac, intratendinous, intraspinal, intracranial, intrathoracic, infusion techniques or intraperitoneally. Furthermore, angiotensinogen can be administered by gene therapy techniques.

The active agents of the invention may be made up in a solid form (including granules, powders or suppositories) or in a liquid form (e.g., solutions, suspensions, or emulsions). The compounds of the invention may be applied in a variety of solutions. Suitable solutions for use in accordance with the invention are sterile, dissolve sufficient amounts of the peptide, and are not harmful for the proposed application. In this regard, the compounds of the present invention are very stable but are hydrolyzed by strong acids and bases. The compounds of the present invention are soluble in organic solvents and in aqueous solutions at pH 5–8.

The active agents may be subjected to conventional pharmaceutical operations such as sterilization and/or may contain conventional adjuvants, such as preservatives, stabilizers, wetting agents, emulsifiers, buffers etc.

The active agents of the invention can be used alone or in a combination of active agents, or may be used in combination with other agents that increase blood flow to ischemic tissue, either via production of new blood vessels (including, but not limited to AII, acidic and basic fibroblast growth factor, transforming growth factor alpha and beta, tumor necrosis factor, platelet-derived growth factor, vascular endothelial growth factor, angiogenin, and haptoglobin), or by stimulating blood flow to ischemic tissue through pre-existing blood vessels, including but not limited to fibroblast growth factor.

For administration, the active agents are ordinarily combined with one or more adjuvants appropriate for the indicated route of administration. The compounds may be admired with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

Formulations suitable for topical administration include liquid or semi-liquid preparations suitable for penetration through the skin (e.g., liniments, lotions, ointments, creams, or pastes) and drops suitable for administration to the eye, ear, or nose.

The dosage regimen for increasing blood flow to ischemic tissue with the active agents of the invention is based on a variety of factors, including the type of injury, the age, weight, sex, medical condition of the individual, the seventy of the condition, the route of administration, and the particular compound employed. Thus, the dosage regimen may vary widely, but can be determined routinely by a physician using standard methods. Dosage levels of the order of between 0.1 ng/kg and 10 mg/kg body weight active agent per body weight are useful for all methods of use disclosed herein.

The treatment regime will also vary depending on the condition of the subject, based on a variety of factors, including the type of injury, the age, weight, sex, medical condition of the individual, the severity of the condition, the route of administration, and the particular compound employed. For example, an active agents is administered to a patient as soon as possible after myocardial infarction for up to 30 days. The therapy is administered for 1 to 6 times per day at dosages as described above.

In a preferred embodiment, the active agent is administered subcutaneously. A suitable subcutaneous dose of active ingredient of active agent is preferably between about 0.1 ng/kg and about 10 mg/kg administered twice daily for a time sufficient to increase blood flow to ischemic tissue. In a more preferred embodiment, the concentration of active agent is between about 100 ng/kg body weight and about 10.0 mg/kg body weight. In a most preferred embodiment, the concentration of active agent is between about 10 μg/kg body weight and about 10.0 mg/kg body weight. This dosage regimen maximizes the therapeutic benefits of the subject invention while minimizing the amount of antagonist needed. Such an application minimizes costs as well as possible deleterious side effects.

For subcutaneous administration, the active ingredient may comprise from 0.0001% to 10% w/w, e.g., from 1% to 2% by weight of the formulation, although it may comprise as much as 10% w/w, but preferably not more than 5% w/w, and more preferably from 0.1% to 1% of the formulation.

In a preferred embodiment, a catheter is placed into the coronary artery of a subject between about immediately after to about 24 hours after myocardial infarction and injecting an effective amount of the active agent into the heart of the subject. The concentration of active agent injected is between about 100 ng/kg body weight and about 10.0 mg/kg body weight, as described above. The injection can be repeated as needed to stimulate increased blood flow in the existing collateral circulation. Injections can also be by other routes, including but not limited to by catheter such via arterial angiography, intracoronary injection, or in a cardioplegic solution by the aortic route. Increased collateral blood flow is determined by standard procedures. For example, collateral flow can be quantified during Chromonar-induced maximum vasodilation and expressed as an ischemic/normal zone (IZ/NZ) ratio. (U.S. Pat. No. 5,244,460 incorporated by reference herein in its entirety) Alternatively, collateral blood flow can be quantitated using radioactive microspheres using a reference flow technique (Dole, et al, Am. J. Physiol., 1982; 243:H371–H378).

In another preferred embodiment of the present invention, the active agent is administered topically. Suitable topical doses and active ingredient concentration in the formulation are as described for subcutaneous administration.

In a further preferred embodiment of all of the aspects of the invention, the active agent is selected from the group consisting of angiotensinogen, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34; SEQ ID NO:35, SEQ ID NO:36, SEQ ID NO:37, SEQ ID NO:38, SEQ ID NO:39, SEQ ID NO:40, SEQ ID NO:41, and SEQ ID NO:42.

In a further aspect, the present invention provides kits to increase blood flow to ischemic tissue, wherein the kits comprise an effective amount of active agent for increasing blood flow to ischemic tissue, and instructions for using the amount effective of active agent as a therapeutic. In a preferred embodiment, the kit further comprises a pharmaceutically acceptable carrier, such as those adjuvants described above. In another preferred embodiment, the kit further comprises a means for delivery of the active agent to a patient. Such devices include, but are not limited to syringes, matrical or micellar solutions, bandages, wound dressings, aerosol sprays, lipid foams, transdermal patches, topical administrative agents, polyethylene glycol polymers, carboxymethyl cellulose preparations, crystalloid preparations (e.g., saline, Ringer's lactate solution, phosphate-buffered saline, etc.), viscoelastics, polyethylene glycols, and polypropylene glycols. The means for delivery may either contain the effective amount of active agent, or may be separate from the compounds, which are then applied to the means for delivery at the time of use.

The present invention may be better understood with reference to the accompanying examples that are intended for purposes of illustration only and should not be construed to limit the scope of the invention.

EXAMPLE 1

Engraftment Of Living-Skin Equivalent

Figure 2:
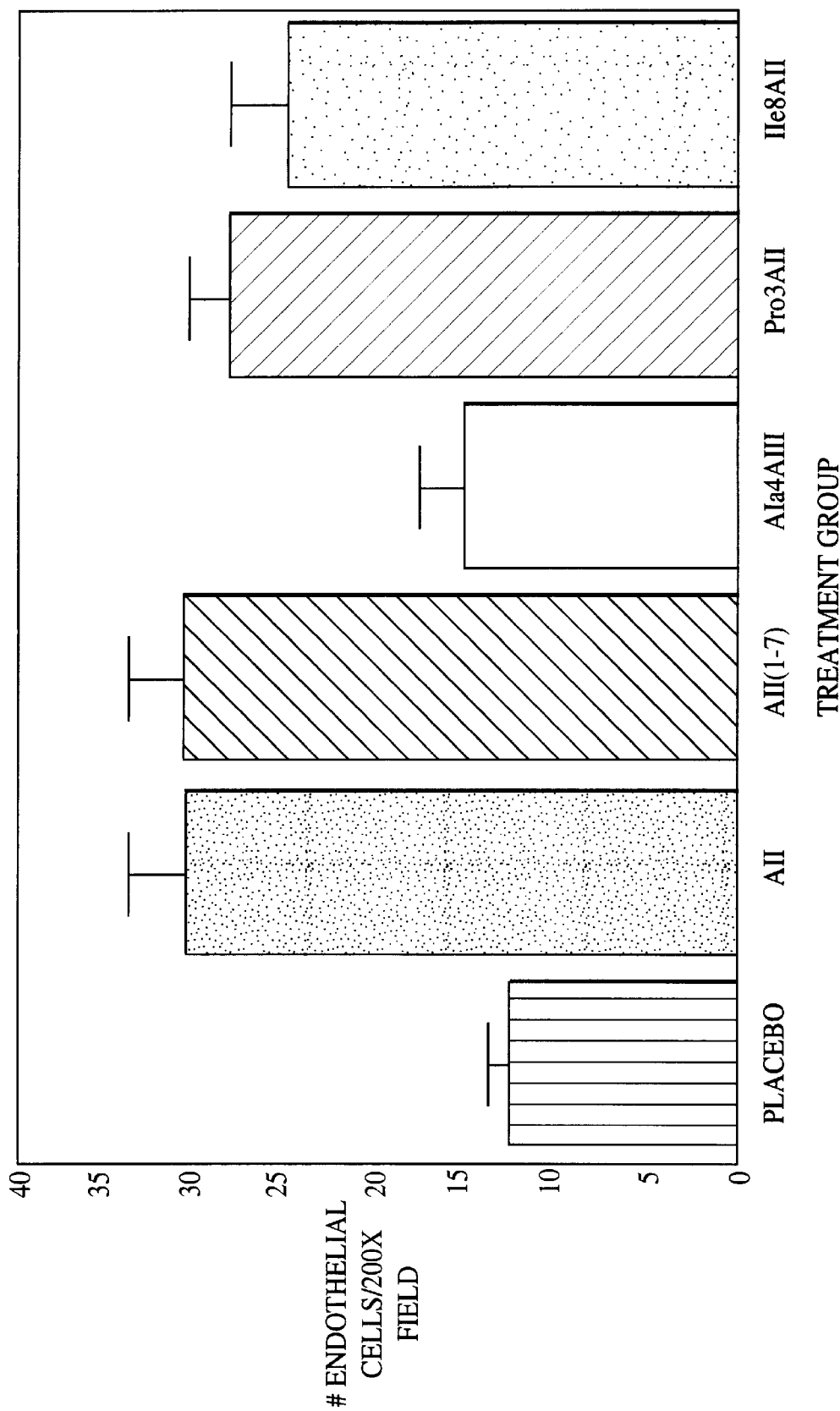
FIG. 2 is a graph showing the effect of AII analogues on endothelial cell production in conjunction with Apligraf treatment.

Male Swiss nude mice (22–24 g) were anesthetized with an intramuscular injection of Ketaset/Rompun and a 1 cm×1 cm full thickness skin excision was made on their dorsal surface. Living skin equivalent (LSE) was placed in the defect and trimmed with microscissors so that no gap was observed between the edges of the mouse skin and the LSE. The mice were divided into 6 groups based upon the peptide tested: (0 [LRS-Dextrose], or 1.0 mg/ml AII or AII analogues, AII(1–7) [SEQ ID NO:4]; Ala4AIII [SEQ ID NO:18]; Pro3AII [SEQ ID NO:31]; and Ile8AII [SEQ ID NO:42]; see Table 3) and the LSE was soaked for 15 minutes in lactated Ringers solution with 5% dextrose with or without peptides prior to placement. After the graft was placed, the dorsal surface of the mouse was covered by petrolatum-embedded gauze followed by two adhesive bandages. After recovery from anesthesia, the mice were returned to their individual cages and observed daily until euthanasia. The mice received intramuscular analgesia for the first three days after surgery. No mouse lost its bandages prior to necropsy or bandage removal on day 7. The mice were necropsied on day 7. At necropsy, the degree of graft take and the appearance of the grafted tissue was noted prior to placement of the biopsy in 10% buffered formalin in preparation for paraffin embedding and section for hematoxylin and eosin staining. The number of endothelial cells and vascular channels were assessed microscopically and the data are presented in FIGS. 1 and 2. These data demonstrate that AII and the AII analogue-treated LSE increased both angiogenesis (vascular channel formation) and endothelial cell production in graft tissue compared to untreated LSE.

TABLE 3

Designation for Analogues/Fragments used in Examples 1-3

| 1GD | Ala$^4$-AII(1–7) | DRVAIHP | SEQ ID NO:38 |
|---|---|---|---|
| 2GD | Pro$^3$-AII(1–7) | DRPYIHP | SEQ ID NO:39 |
| 5GD | Lys3-AII(1–7) | DRKYIHP | SEQ ID NO:40 |
| 9GD | NorLeu3-AII(1–7) | DR(nor)YIHP | SEQ ID NO:41 |
| AII(1–7) | | DRVYIHP | SEQ ID NO:4 |
| AII | | DRVYIHPF | SEQ ID NO:1 |
| | Ala4-AIII | RVYAHPF | SEQ ID NO:18 |
| | Pro3-AII | DRPYIHPF | SEQ ID NO:31 |
| | Ile8-AII | DRVYIHPI | SEQ ID NO:42 |

EXAMPLE 2

Partial Thickness Thermal Injury Model

Animals

Thirty-six male Hartley guinea pigs weighing approximately 500 grams were purchased from Charles Rivers Laboratory (Charles Rivers Mass.). The guinea pigs were housed in a 12:12 hour light:dark, cycle in the USC Vivaria. Food and water were available ad libitum.

Surgical Procedures

The guinea pigs were anesthetized by intramuscular injection of 14 mg/kg Rompun and 130 mg/kg Ketamine. Hair was then removed from the dorsal surface through shaving with animal clippers followed by treatment with a thioglycollate depilatory. After hair removal the area was scrubbed with betadine twice followed by 70% ethanol. Two burns were produced on each guinea pig with an 18 mm solid brass rod, which was warmed in a 75° C. water bath. One end of the brass rod was placed on the back of the guinea pig for 50 seconds. This procedure was repeated with different brass rods for each animal and each burn.

Each burn was treated with 10% low-viscosity CMC with and without 1 mg/ml AII, AII analogue or fragment (0 [LRS-Dextrose], or 1.0 mg/ml AII or AII analogues, AII (1–7) [SEQ ID NO:4]; Ala4AIII [SEQ ID NO:18]; Pro3AII [SEQ ID NO:31]; or Ile8AII [SEQ ID NO:42]) in 0.05 mol/L phosphate buffer, pH 7.3, and was individually dressed with a Hilltop Chamber and covered with Tegaderm. The bandages were checked and changed daily for the first 5 days and every other day until necropsy on day 7 after injury. The guinea pigs were given 20 µg/kg buprenex (buprenorphine hydrochloride) intramuscularly for pain on the day of injury and the first 3 days after injury.

Validation with India Ink Injection

Initial studies were conducted in which the depth of the burn was evaluated with intraaortic injection of India Ink. One or 2 days after initiation of the thermal injury, the guinea pigs were anesthetized with intramuscular ketamine and rompun. The ascending thoracic aorta was cannulated, and 60 ml India Ink was injected through the cannula under 500 mm Hg. This pressure was used to ensure filling of all patent vessels. After the India Ink was injected the animals were sacrificed, and the injury sites were excised and placed in 10% buffered formalin and prepared for histologic evaluation. The histologic sections from these preparations were examined to evaluate the depth of necrosis and capillary ischemia.

Histologic Evaluation

On day 7 after thermal injury, the guinea pigs were euthanized, the burned areas were excised en bloc and the tissues were placed in 10% buffered formaldehyde solution overnight. The tissues were embedded in paraffin, and 5 µm sections were prepared. The sections were processed for immunohistochemical analysis with a primary antibody to cyclin (MIB-1) (AMAC, Westbrook, Mass.) followed by recognition of the primary antibody with a DAKO kit (DAKO, Santa Barbara, Calif.) used as described below.

The paraffin-embedded sections were baked in an oven overnight at 60° C. Deparaffinization was performed by four 5-minute incubations in "fresh" xylene followed by two 5-minute incubations with 100% ethanol, two 5-minute incubations with 95% ethanol, and one 5-minute incubation with $H_2O$. Endogenous peroxidase activity was then quenched with 0.3% $H_2O_2$ in $H_2O$. Antigen retrieval was performed following the protocol of Shi et al. with minor modifications. In brief, the slides were placed in plastic coplin jars in 5% urea in 0.1 mol/L Tris buffer (pH 9.0). The slides were then placed in a microwave oven and set at maximal power for 3 minutes. The antigen retrieval solution was replenished with distilled water when evaporation was excessive and were microwaved again for 5 minutes at 50% power. The slides were then allowed to cool for 10 minutes and were placed in phosphate-buffered saline solution (PBS) for 5 minutes.

Immunohistochemical staining was performed with the avidin-blotin-peroxidase conjugate method with some modifications. The slides were placed in a PBS bath for 5 minutes and then laid in humidified incubation chambers. Blocking for nonspecific antibody binding was performed by incubating the sections in 5% horse serum in PBS. The solution was decanted and replaced with the solution of primary antibody. The primary antibody, MIB-1, was used at a dilution of 1:100 in PBS and was incubated for 60 minutes at room temperature. The slides were washed with PBS for 5 minutes and were then incubated with the secondary biotinylated horse-anti-mouse antibody. After a 5-minute wash in PBS the avidin-biotin complex was applied to slides at a dilution of 1:100 in PBS at room temperature and was incubated for 1 hour.

After a final rinse in PBS, the sections were incubated in 0.06% 3,3'-diaminobenzidine in PBS with 0.03% hydrogen peroxide for 5 minutes. After a counterstain was performed in modified Harris' hematoxylin-eosin the sections were dehydrated and coverslipped with Permount.

With an Olympus Vanox-S AH-2 dissecting microscope and a magnification power of 100×, each section of the biopsy specimen was separated into either areas on the burn edge or the actual burn areas. The area of the burn was excised and serially cut into three to five sections 4 to 5 mm in thickness. The entire area of the burn and edge of the burn was embedded and examined histologically. In each section four to six consecutive medium-power fields (mpf, 100×) were evaluated. The cells that stained with the MIB-1 antibody were a distinct brown color. All stained cells located within the hair follicles of the biopsy sections were counted. To count the MIB-1 stained cells each section on the slide was separated into individual medium power fields (mpf). Each field was then determined to be either a section on the edge of the burn or a part of the burn area itself. An edge was indicated by a positive stain showing brown epithelial cells along the edge of the section. A burn area was indicated by an absence of brown staining cells along the edge. The brown cells located within each hair follicle were counted one at a time under mpf magnification. To move to the next mpf a landmark was established, and the slide was then moved to the next adjacent field.

All animals survived the burn procedures and did not demonstrate evidence of significant discomfort throughout the study interval. The depth of the burns was determined to be deep partial-thickness to full-thickness by (1) analysis of vessel patency with intraaortic injection of India Ink and (2) the appearance of the cells in the hair follicles by microscopic analysis of hematoxylin-eosin-stained sections. This analysis revealed most of the preexisting blood vessels and cells were destroyed in the burn site, although the injuries did not extend through the panniculus carnosus.

Figure 3:
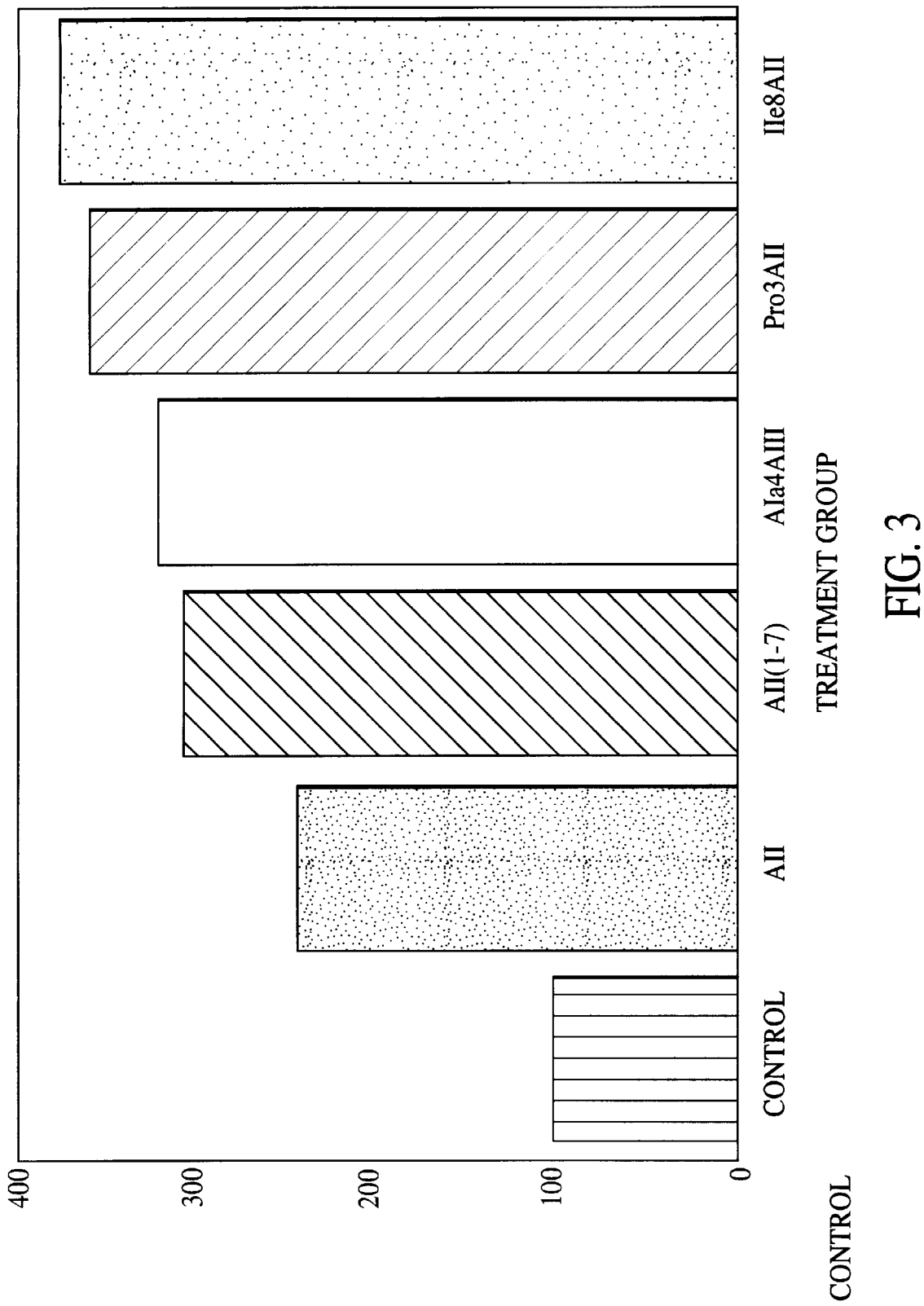
FIG. 3 is a graph showing the effect of AII analogues on blood flow after thermal injury.

FIG. 3 demonstrates the effect of AII and the same AII analogues used in Example 1 on angiogenesis after thermal injury. These data demonstrate that treatment of the burn areas with the AII and AII analogues produces an increased blood flow response compared to control, with the AII analogues showing an increased blood flow response compared to AII.

EXAMPLE 3

Effect of Angiotensin Peptides on the Formation of Collateral Circulation in Ischemic Myocardial Tissue Rabbits underwent a surgical procedure under intramuscular anesthesia (Ketamine and Rompum) after shaving with animal clippers and preparation with betadine and isopropyl alcohol. A midline sternotomy was performed. After exposure of the pericardial sac, a three centimeter incision was made into the pericardium. After visualization of the epicardial surface, two coronary arteries, the left circumflex and the left anterior descending arteries, were exposed and ligated by 4-0 Vicryl suture. Vehicle (10% Hydron, 60% ethanol and 1% polyethylene glycol), with or without peptide (1 mg/ml, 0.05 ml) was injected in the cardiac muscle distal to the site of coronary occlusion. The sternum was then closed with 2-0 Silk. The muscle and skin were then closed with 3-0 Dexon II suture. Starting at 7 days after surgery, the animals were euthanized and necropsies performed. The number of blood vessels present in the infarct site was assessed grossly and by microscopic evaluation. The presence of a blood vessel was defined as a channel lined with endothelial cells that contained red blood cells (indicating that the vessels had a blood source).

All peptides (AII, AII(1–7), 1GD, 2GD, 5GD and 9GD: see table 2) tested increase vascularization of the infarct site. The increases ranged from approximately 4 fold to approximately 14 fold increase in the formation of collateral circulation after ligation of the artery. The data collected from microscopic examination of multiple tissue sections are in Table 4.

TABLE 4

Effect of Angiotensin Peptides on the Foundation of Collateral Circulation in Ischemic Myocardial Tissue

| Treatment | # of Animals | Mean ± SEM | P Value |
| --- | --- | --- | --- |
| Hydron | 7 | 5.67 ± 0.74 | |
| 1GD | 4 | 23.4 ± 8.6 | 0.020 |
| 2GD | 2 | 31.2 ± 5.62 | <0.001 |
| 5GD | 2 | 24.55 ± 2.34 | <0.001 |
| 9GD | 3 | 21.2 ± 2.8 | <0.001 |
| AII | 4 | 29.8 ± 12.3 | <0.001 |
| AII(1–7) | 2 | 80.6 ± 4.5 | <0.001 |

The methods and kits of the present invention, by increasing blood flow to ischemic tissue, significantly enhance the utility of presently available treatments for ischemia, and particularly benefit treatments for skin and heart ischemia, and significantly benefit tissue grafting by increasing blood flow to tissue grafts.

It is to be understood that the invention is not to be limited to the exact details of operation, or to the exact compounds, compositions, methods, procedures or embodiments shown and described, as obvious modifications and equivalents will be apparent to one skilled in the art, and the invention is therefore to be limited only by the full scope of the appended claims.

We claim:

1. A method for increasing blood flow to ischemic cardiac tissue comprising the administration of an amount effective for increasing blood flow to ischemic cardiac tissue of at least one active agent comprising a sequence selected from the group consisting of angiotensinogen, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42.

2. A kit for increasing blood flow to ischemic cardiac tissue, comprising:
   (a) an amount effective for increasing blood flow to ischemic cardiac tissue of at least one active agent comprising a sequence selected from the group consisting of angiotensinogen, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42 and;
   (b) instructions for using the amount effective of active agent for increasing blood flow to ischemic cardiac tissue.

3. The kit of claim 2 further comprising a means for delivery of the active agent.

4. A method for increasing blood flow to ischemic cardiac tissue comprising the administration of an amount effective for increasing blood flow to ischemic cardiac tissue of at least one active agent comprising a sequence selected from the general formula:

R1-Arg-R2-R3-R4-His-Pro-R5, wherein
R1 is Asp or is absent;
R2 is selected from the group consisting of Val, Ala, Ile, Pro, Lys, Norleu, and Leu;

R3 is selected from the group consisting of Ala, Tyr, and Tyr(PO$_3$)$_2$;

R4 is selected from the group consisting of Val, Ala, Ile, Norleu, and Leu;

R5 is Phe, Ile, or is absent; and wherein the active agent is not AII.

5. The method of claim 4 wherein the active agent is selected from the group consisting of SEQ ID NO:4, SEQ ID NO:19, SEQ ID NO:24, SEQ ID NO:26, SEQ ID NO:31, SEQ ID NO:32, SEQ ID NO:33, SEQ ID NO:34, SEQ ID NO:38, SEQ ID NO:39, SEQ ID NO:40, SEQ ID NO:41, and SEQ ID NO:42.

6. A kit for increasing blood flow to ischemic cardiac tissue, comprising:

(a) an amount effective for increasing blood flow to ischemic cardiac tissue of at least one active agent comprising a sequence selected from the general formula R1-Arg-R2-R3-R4-His-Pro-R5, wherein R1 is Asp or is absent;

R2 is selected from the group consisting of Val, Ala, Ile, Pro, Lys, Norleu, and Leu;

R3 is selected from the group consisting of Ala, Tyr, and Tyr(PO$_3$)$_2$;

R4 is selected from the group consisting of Val, Ala, Ile, Norleu, and Leu;

R5 is Phe, Ile, or is absent;

wherein the active agent is not AII; and (b) instructions for using the amount effective of active agent for increasing blood flow to ischemic cardiac tissue.

7. The kit of claim 6 wherein the active agent is selected from the group consisting of SEQ ID NO:4, SEQ ID NO:19, SEQ ID NO:24, SEQ ID NO:26, SEQ ID NO:31, SEQ ID NO:32, SEQ ID NO:33, SEQ ID NO:34, SEQ ID NO:38, SEQ ID NO:39, SEQ ID NO:40, SEQ ID NO:41, SEQ ID NO:42.

8. The kit of claim 6, further comprising a means for delivery of the active agent.

* * * * *